United States Patent [19]

Turner

[11] Patent Number: Plant 6,487

[45] Date of Patent: Dec. 27, 1988

[54] ANIGOZANTHOS PLANT NAMED BUSH GLOW

[75] Inventor: Mervyn L. Turner, Monbulk, Australia

[73] Assignee: Biotech Plants Pty. Ltd., Somersby, Australia

[21] Appl. No.: 33,814

[22] Filed: Apr. 3, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Kangaroo Paw plant (genus Anigozanthos) named Bush Glow characterized by the indumentum of the flower stem being bronze, the ovary red, and the perianth orange; short broad green leaves; Spring and Summer flowering in outdoor warm temperate climate, and superior resistance to Alternaria species.

1 Drawing Sheet

The present invention relates to a new and distinctive cultivar of Anigozanthos (Kangaroo Paw), named Bush Glow. Kangaroo Paw is the popular name applied to all species of the botanical genera Anigozanthos Labill and Macropidia Harv and their variants and hybrids.

Anigozanthos Labill is a genus of eleven described species of herbaceous perennial plants of the family Haemodoraceae, and which are endemic to the southwestern region of western Australia. These species, together with the closely allied monotype *Macropidia fuliginosa* (Hook.) Druce, are as above noted jointly referred to by the popular common name Kangaroo Paws.

Wild populations of Kangaroo Paws grow in a warm temperate Mediterranean climate (Summer drought). Vitality is at a minimum in late Summer/early Autumn, and some species show or tend to a full deciduous dormancy at this time. Active vegetative growth is reinstated with the onset of lower temperatures and rainfall in the Autumn (Fall). The flowering season varies considerably between species, but the display period is normally of several months somewhere within the range of late Winter to mid Summer.

Mature plants consist of a clump of leaf fans arising from ramified rhizome which exists at immediate subsurface soil levels. Rhizome extends and branches by annual growth and is more or less persistent. Leaves and roots are replenished on an annual basis.

Leaves arise from rhizome buds and exist as fans of alternate ensheathing leaves arranged on an equitant conduplicate pattern, and with very short internodes.

Individual leaves are normally relatively straight and narrow in length, being approximately parallel sided in the lower half or more, and tapering to an acute point above. As new leaves arise in the center of each fan between the next youngest leaves, older leaves are progressively displaced at an angle. In some species older leaves may become distinctly recurved.

There is variation between species in the stature of leaf fans and in the relative width of individual leaves. In the largest species, leaves may be one meter in length and up to five centimeters wide. In the smallest species, leaves may be ten centimeters in length and one centimeter wide.

The active apical meristem in a leaf fan is located near the base of the fan during the active vegetative growth stage. Eventually, a rapid increase in length of successive internodes occurs accompanied by a decrease in leaf size and followed by a differentiation of the apex, the overall process forming a flower stem. The overall length of the flower stem varies between 1.5 and 2.5 times the length of the basal leaves of the leaf fan according to species.

The inflorescence per se is a unilateral raceme, both series of sub-sessile to shortly pedunculate alternating flowers being oriented in the same direction. Each peduncle is marked by a pointed bract shorter than the flower. The flower is itself bilaterally symmetrical consisting of a spherical tri-locular basal ovary extending into an initially narrower and cylindrical perianth which broadens and flattens and terminates in six lobes. At anthesis the lobes which are contiguous in bud, separate and reflex, the degree varying with species. The style is simple, free, and about as long as the perianth, and terminates in a small sub spherical stigma. The six anthers have short to very short filaments, the points of insertion being towards the apex of the perianth.

Three more or less distinctive patterns in the architecture of the flower stem can be recognized. In some species the architecture is simple, with the stem being simple and terminating in a solitary raceme. In other species, the stem is initially simple but forks immediately sub-terminally, each fork terminating in a raceme. In some species, the stem is initially simple but then branches more or less dichotomously, the node being subtended by a shortened leaf. Secondary branching may occur, but eventually most branches fork, each ultimate branch or fork terminating in a raceme.

In one extreme in some species, the length of the overall flower stem can exceed two meters. At the other extreme, in some species, the stem may rarely be longer than twenty centimeters.

Racemes may be few to many flowered and individual flowers from three centimeters to ten centimeters in length varying with species.

In all species the flowers, and in all but one species the stem, are clothed with a close indumentum of velvet texture. The indumentum is colored and the stem, ovary, and perianth may be distinctively colored. Flower color or pattern of coloration normally applies to that of this indumentum. Development of pigmentation is to some degree a function of environmental conditions, especially of temperature and total irradiance during bud development.

The new cultivar Bush Glow was created by the inventor as a result of a controlled crossing of a selected genotype of the species *Anigozanthos humilis* Lindl (seed parent) with a selected genotype of the species *Anigozanthos flavidus* DC (pollen parent).

Asexual reproduction by applicant in Monbulk, Victoria, Australia by divisions of the rhizome and by aseptic multiplication of leaf shoots including apical meristem on nutrient media has reproduced the unique features of the new cultivar through successive generations.

The following characteristics distinguish Bush Flame from both its parents and from other Kangaroo Paws known and used in the ornamental horticultural industry.

1. The cultivar exhibits superior resistance to Alternaria species; both parents were themselves selected as genotypes with superior resistance when compared with other varieties within the respective species.

2. The flower stem of the cultivar is normally sub-terminally forked, only rarely branched. The length of the overall inflorescence is typically in the range of 60 cm to 80 cm, contrasting with both parents. The flower stem of the seed parent is normally simple with a single terminal raceme, and is rarely longer than 40 cm. The flower stem of the pollen parent is branched and normally sub-terminally forked, each fork with a raceme of flower, and the length of the overall flower stem is typically in the range of 120 cm to 160 cm.

3. The color of the indumentum of the stem is bronze, the ovary red, and the perianth orange. This contrasts with the seed parent where the indentum is yellow, and the pollen parent where the indentum is orange-red but confined to the ovary and perianth only.

4. The foliage is of similar color and as broad as in the pollen parent, but not as long. The foliage of Bush Glow differs from that of the seed parent which is shorter and narrower, and distinctly recurved.

5. The cultivar is vigorous in vegetative growth, and flowers are produced over Spring and Summer months in outdoor warm temperate environments.

The accompanying colored photographs illustrate the new cultivar, with the colors being as true as it is reasonably possible to obtain in colored reproductions of this type. The photograph at the top is a perspective view of a plant of Bush Glow, and the photograph at the bottom is an enlarged showing of the flower.

The following is a detailed description of Bush Glow based on plants produced at Bush Gems Garden Nursery in Monbulk, Victoria, Australia. Color references are made to the Royal Horticultural Society Colour Chart except where general color terms of ordinary dictionary significance are used. Terms used have the same meaning and significance as those used and defined above regarding the characteristics of propagation, plant form, habit of growth, foliage, flowers and rhizome common and general to all plants of Anigozanthos.

Parentage: A hybrid of *Anigozanthos humilis* (seed parent, selected clone) and *Anigozanthos flavidus* (pollen parent, selected clone).

Propagation: Asexual by: (A) Rhizome divisions. Optimum period late Summer to early Fall. (B) "In vitro" proliferation of multiple shoots from plants of apical meristem with immediate leaf primordia, with a five-fold multiplication in four weeks on appropriate media. Rooting in three to five weeks at approximately 20 degress Celcius root zone temperature in high relative humidity environment. Use of anti-transpirant sprays beneficial.

Plant description:

(A) *Form.*—Clumping, rhizomic, perennial plant suited to cultivation in containers, in gardens (in essentially frost free environments), and as a row-crop cut flower. Clumps are relatively dense.

(B) *Habit of growth.*—The main period of active growth — rhizome extension, production of new leaf fans, and induction/evocation of flower — is Winter and Spring, but with irrigation in a suitable enviroment growth can continue year-round.

(C) *Foliage.*—The basal leaves of each leaf fan are of alternate, conduplicate, ensheathing arrangement. (1) Size and shape: Variable according to environmental conditions but normally up to 35 cm in length and 1.5 cm in width at base, parallel edges in lower half, tapering to a point in upper half. (2) Texture: Smooth, glabrous, except for scattered hairs along edges of leaves. (3) Color: Mature, healthy foliage is green 141B. The main floral axis bears widely spaced leaves of diminishing size, the lowermost similar to basal leaves but rarely longer than 20 cm, reducing progressively to approximately 6 cm. With reduction in length there is a progressive increase in the development of a hairy indumentum. Color same as basal leaves.

Flowers:

(A) *Flowering habit.*—Flowers in dense, unilateral biseriate terminal racemes. The floral stem is occasionally branched and almost always subterminally forked, with each ultimate pedicel bearing a raceme. The overall length rarely is greater than 80 cm and is typically in the range 60 to 80 cm.

(B) *Natural flowering season.*—Spring and early Summer; young plants produced from tissue culture may have an atypical first flowering season.

(C) *Flower bud.*—Sub-cylindrical; immediately prior to opening approximately 30 mm long and 6 mm diameter; the Anterior lobes of the perianth are fused in a pointed asymmetrical tip; color is similar to color of flowers.

(D) *Flowering raceme.*—Straight axis, the pedicels of the flowers short, approximatley 2 mm, spaced at approximately 12 mm intervals, each pedicel subtended by a small narrow bract, approximately 2 mm wide and 12 mm long. The lowest flowers of the raceme open first, buds at the anterior end progressively grow and open. A single raceme typically produces 20 to 30 flowers.

(E) *Individual flower.*—Sub-spherical basal ovary approximately 12 mm in diameter, extending into a sub-tubular perianth, approximately 25 mm in length. The ultimate 12 mm of the perianth consists of six lobes which open and partly reflex away from the floral axis at maturity, before again closing.

(F) *Color.*—The indumentum of the peduncle is gray-orange 177A, the pedicels and ovary of the flowers red 47B, the perianth greyed orange 163B.

Disease resistance: Resistance to fungal leaf diseases (viz. Alternaria spp.) is superior to typical wild seedling Kangaroo Paws, as confirmed by field trials at various sites and seasons.

I claim:

1. A new and distinct cultivar of Anigozanthos plant named Bush Glow, as described and illustrated, and parts thereof.

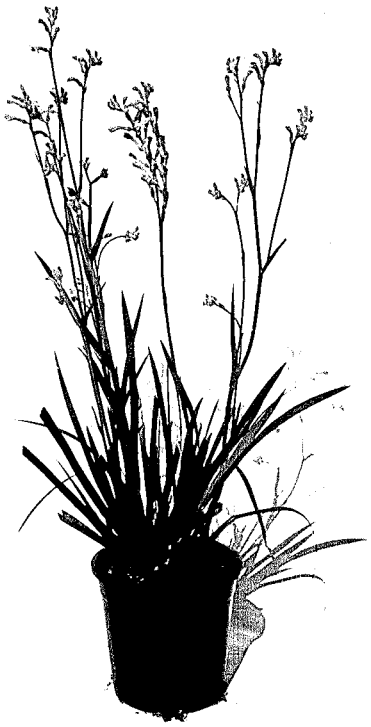
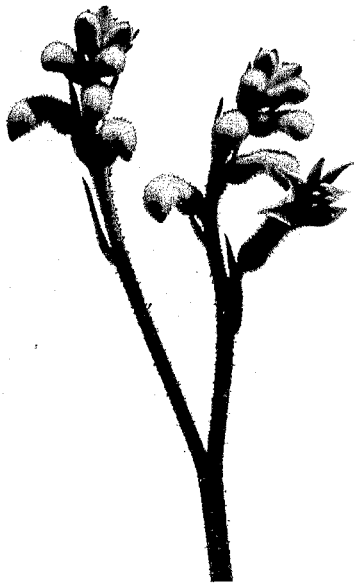

* * * * *